US008911735B2

(12) United States Patent
Fung et al.

(10) Patent No.: US 8,911,735 B2
(45) Date of Patent: *Dec. 16, 2014

(54) COMPLEMENT INHIBITORS AND USES THEREOF

(75) Inventors: Michael S. C. Fung, Gaithersburg, MD (US); Cecily R. Y. Sun, Bellaire, TX (US); William N. C. Sun, Bellaire, TX (US)

(73) Assignee: Genentech, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/524,465

(22) Filed: Jun. 15, 2012

(65) Prior Publication Data
US 2012/0251549 A1    Oct. 4, 2012

Related U.S. Application Data

(60) Division of application No. 13/045,895, filed on Mar. 11, 2011, now Pat. No. 8,221,756, which is a continuation of application No. 10/908,738, filed on May 24, 2005, now Pat. No. 7,927,592, which is a division of application No. 09/816,839, filed on Mar. 23, 2001, now Pat. No. 6,998,468.

(60) Provisional application No. 60/191,429, filed on Mar. 23, 2000.

(51) Int. Cl.
*A61K 39/395* (2006.01)
*C07K 16/40* (2006.01)
*A61K 39/00* (2006.01)

(52) U.S. Cl.
CPC ............... *C07K 16/128* (2013.01); *C07K 16/40* (2013.01); *C07K 2317/55* (2013.01); *C07K 2317/24* (2013.01); *A61K 2039/505* (2013.01)
USPC .................................................... 424/145.1

(58) Field of Classification Search
None
See application file for complete search history.

(56) References Cited

U.S. PATENT DOCUMENTS

| 4,946,778 | A | 8/1990 | Ladner et al. |
| 5,225,539 | A | 7/1993 | Winter |
| 5,530,101 | A | 6/1996 | Queen et al. |
| 5,861,156 | A | 1/1999 | George et al. |
| 6,998,468 | B2 | 2/2006 | Fung et al. |
| 7,927,592 | B2 | 4/2011 | Fung et al. |
| 8,221,756 | B2 | 7/2012 | Fung et al. |

FOREIGN PATENT DOCUMENTS

| WO | WO 96/09043 A1 | 3/1996 |
| WO | WO 01/70818 | 9/2001 |

OTHER PUBLICATIONS

Amsterdam, et al., 1995, "Limitation of Reperfusion Injury by a Monoclonal Antibody to C5a during Myocardial Infarction in Pigs", Am. J. Physiol. 268:H448-H457.
Anderson, et al., 1987, "A Monoclonal Antibody Against Human Complement Component C2", Biochem. Soc. Trans., vol. 15, No. 4, pp. 660-661.
Brouwer et al, 2006, "Mannan-binding lectin (MBL)-mediated opsonization is enhanced by the alternative pathway amplification loop." Molec. Immunol 43:2051-2060.
Canfield, et al., 1991,"The Binding Affinity of Human IgG for its High Affinity Fc Receptor is Determined by Multiple Amino Acids in the C2 Domain and is Modulated by the Hinge Region", J. Exp. Med. 173:1483-1491.
Chikako, et al., 1986, "Monoclonal Anti-Human C4b Antibodies: Stabilization and Inhibition of the Classical Pathway C3 Convertase", Molecular Immunology, vol. 23, No. 2, pp. 151-157.
Datta, 1988, "Murine Lupus", Meth. Enzymol. 162:385-413.
Evans, et al., 1995, "Rapid Expression of an Anti-Human C5 Chimeric Fab Utilizing a Vector That Replicates in COS and 293 Cells", J. Immunol. Meth. 184:123-138.
Fitch, et al., 1999, "Pharmacology and Biological Efficacy of a Recombinant, Humanized, Single-Chain Antibody C5 Complement Inhibitor in Patients Undergoing Coronary Artery Bypass Graft Surgery with Cardiopulmonary Bypass", Curculation 100:2499-2506.
Fletcher, et al., 1993, "C5a-Induced Myocardial Ischemia: Role for CD-18-Dependent PMN Localization and PMN-Platelet Interactions", Am. J. Pathsiol. 265:h1750-1761.
Frank et al., Fundamental Immunology, $2^{nd}$ edition, edited by W. Paul. Raven Press, New York pp. 679-701.
Hans-Peter Heinz, et al., 1989, "Monoclonal Antibodies Against Components of the Classical Pathway of Complement", Complement Inflamm. 6: 166-174.
Holers, 1996, "Complement", In: Clinical Immunology: Principles and Practice, R.R. Rich Ed., Mosby Press, 1996, pp. 383-391.
Homeister, et al., 1993, "Soluble Complement Receptor Type 1 Prevents Human Complement-Mediated Damage of the Rabbit Isolated Heart", J. Immunol. 150: 1055-1064.
Ichihara et al., 1986, "Monocloncal anti-human C4b antibodies: stabilization and inhibition of the classical-pathway C3 convertase." Molec. Immunol. 23(2): 151-7.

(Continued)

*Primary Examiner* — Sharon Wen
(74) *Attorney, Agent, or Firm* — Jones Day

(57) ABSTRACT

The invention relates to C2a inhibitors, which bind to C2a and block the functional activity of C2a in complement activation. The inhibitors include antibody molecules, as well as homologs, analogs and modified or derived forms thereof, including immunoglobulin fragments like Fab, $F(ab')_2$ and Fv, small molecules, including peptides, oligonucleotides, peptidomimetics and organic compounds. A monoclonal antibody, which bound to C2a and blocked its ability to activate complement was generated and designated 175-62. The hybridoma producing this antibody was deposited at the American Type Culture Collection, 10801 University Blvd., Manassas, Va. 20110-2209, under Accession Number PTA-1553.

8 Claims, 4 Drawing Sheets

(56) References Cited

OTHER PUBLICATIONS

Inal et al., 1999, "Schistosoma TOR (trispanning orphan receptor), a novel, antigenic surface receptor of the blood-dwelling, Schistosoma parasite", Biochem. Biophys. ACTA 14445(3):283-298.
Inal et al., 2000, "A Schistosoma protein, Sh-TOR, is a novel inhibitor of complement which binds human C2", FEBS Letter 470:131-134.
Janeway et al., 1997, Immunobiology, 3$^{rd}$ Ed., Current Biology Ltd. England, pp. 133:7-8.
Kohler and Milstein, 1975, "Continuous Cultures of Fused Cells Secreting Antibody of Predefined Specificity", Nature 256: 495-497.
Kroshus, et al. 1995, "Complement Inhibition with an Anti-C5 Monoclonal Antibody Prevents Acute Cardiac Tissue Injury in an Ex Vivo Model of Pig-To-Human Xenotransplantation", Transplantation 60:1194-1202.
Lambris et al., 2008, "Complement evasion by human pathogens." Nat. Rev. Microb 6:132-142.
Lazar, et al., 1999, "Total Complement Inhibition: An Effective Strategy to Limit Ischemic Injury During Coronary Revasculaization on Cardiopulmonary Bypass", Circulation 100:1438-1442.
Matsushita, 1996, "The Lectin Pathway of the Complement System", Microbiol. Immunol. 40(12):887-893.
Matsushita, et al., 1998, "MASP-1 (MBL-Associated Serine Protease-1)", Immunobiol. 199:340-347.
Morgan, 1994, "Clinical Complementology: Recent Progress and Future Trends", Eur. J. Clin. Invest. 24:219-228.
Mulligan, et al., 1992, "Protective Effects of Soluble CR1 in Complement- and Neutrophil-Mediated Tissue Injury", J. Immunol. 148:1479-1485.
Nagasawa, et al., 1977, "Cleavage of C2 by C1s into Antigenically Distinct Fragments C2a and C2b: Demonstration of Binding of C2b and C4b", Proc. Natl. Acad. Sci. (USA) 74:2998-3001.
Oglesby, et al., 1988, "Evidence for a C4b Binding Site on the C2b Domain of C2", J. Immunol. 141:926-931.
Pulito, et al., 1996, "Humanization and Molecular Modeling of the Anti-CD4 Monoclonal Antibody, OKT4A", J. Immunol. 156:2840-2850.
Rabinovici, et al., 1992, "Role of Complement in Endotoxin/Platelet-Activating Factor-Induced Lung Injuy", J. Immunol. 149:1744-1750 (1992).
Riechmann, et al., 1988, "Reshaping Human Antibodies for Therpay", Nature 332:323-327.
Rinder, et al., 1995, "Blockade of C5a and C5b Generation Inhibits Leukocyte and Platelet Activation During Extracorporeal Circulation", J. Clin. Invest. 96:1564-1572.
Salvant, et al., 1988, "Experimental Glomerulonephritis", Meth. Enzymol. 162:421-461.
Schlinder, et al., 1990, "Recombinant C5a Stimulates Transcription Rather Then of Interleukin-1 (IL-1) and Tumor Necrosis Factor: Translational Signal Provided by Lipopolysaccharide or.IL-1 Itself", Blood 76:1631-1638.
Stenbaeck, et al., 1986, "Human Complement Component C2: Production and Characterization of Polyclonal and Monoclonal Antibodies Against C2", Mol. Immunol. 23:879-886.
Stoltzner et al. "Temporal accrual of complement proteins in amyloid plaques in Down's syndrome with Alzheimer's disease ", Am J Pathol. 156(2):489-499.
Suankratay et al., 1998, "Requirement for the alternative Pathway as well as C4 and C2 in complement-dependent hemolysis via the lectin pathway." J. Immunol. 160:3006-3013.
Suankratay, et al., 1989, "Mechanism of Complement-Dependent Haemolysis via the Lection Pathway: Role of the Complement Regulatory Proteins", Clin. Exp. Immunol. 117:442-448.
Suankratay, et al., 1998, "Complement Regulation in Innate Immunity and the Acute-Phase Response: Inhibition of Mannan-Binding Lectin-Initialed Complement Cytolysis of C-Reactive Protein", Clin. Exp. Immunol. 113:353-359.
Vakeva et al., 1998, "Myocardial infarction and apoptosis after myocardial ischemia and reperfusion: role of the terminal complement components and inhibition by anti-C5 therapy", Circulation 97:2259-2267.
Vorup-Jensen, et al., 1998, "MASP-2, the C3 Convertase Generating Protease of the MBLectin Complement Activating Pathway", Immunobiol. 199: 348-357.
Wang, et al., 1995, "Anti C5 Monoclonal Antibody Therapy Prevents Collagen-Induced Arthritis and Ameliorates Established Disease", Proc. Natl. Acad. Science (USA) 92:8955-8959.
Wang, et al., 1996, "Amelioration of Lupus-Like Autoimmune Disease in NZB/W F.sub.1 Mice After Treatment With a Blocking Monoclonal Antibody Specific for Complement Component C5", Proc. Natl. Acad. Sci. (USA), 93:8563-8568.
Weisman, et al., 1990, "Soluble Human Complement Receptor Type 1: In Vivo Inhibitor of Complement Suppressing Post-Ischemic Myocardial Inflammation and Necrosis", Science 249:146-151.
Wiedmer et al., 1991, "Participation of Protein Kinases in Complement C5b-9-Induced Shedding of Platelet Plasma Membrane Vesicles", Blood 78:2880-2886.
Xu et al., 1994, "Residue at Position 331 in the IgG1 and IgG4 C2 Domains Contributes to Their Differential Ability to Bind and Activate Complement", J. Biol. Chem. 269:3469-3474 (.
Zhang, et al., 1999, "Calcium-Indepentent Haemolysis via the Lectin Pathway of Complement Activation in the Guinea-Pig and Other Species", Immunol. 97:686-692.
Zhang, et al., 1999, "Lysis via the Lectin Pathway of Complement Activation: minireview and lectin pathway enhancement of endotoxin-initialed hemolysis", Immunopharmacol. 42:81-90.
Non-final Office Action issued on Nov. 18, 2002 in the prosecution history of U.S. Appl. No. 09/816,839.
Final Office Action issued on May 19, 2003 in the prosecution history of U.S. Appl. No. 09/816,839.
Non-final Office Action issued on Dec. 4, 2003 in the prosecution history of U.S. Appl. No. 09/816,839.
Final Office Action issued on Jun. 4, 2004 in the prosecution history of U.S. Appl. No. 09/816,839.
Notice of Allowance issued on Feb. 25, 2005 in the prosecution history of U.S. Appl. No. 09/816,839.
Non-final Office Action issued on Apr. 7, 2008 in the prosecution history of U.S. Appl. No. 10/908,738.
Non-final Office Action issued on Aug. 6, 2008 in the prosecution history of U.S. Appl. No. 10/908,738.
Non-final Office Action issued on Jun. 23, 2010 in the prosecution history of U.S. Appl. No. 10/908,738.
Notice of Allowance issued on Dec. 14, 2010 in the prosecution history of U.S. Appl. No. 10/908,738.
Non-final Office Action issued on Sep. 21, 2011 in the prosecution history of U.S. Appl. No. 13/045,895.
Notice of Allowance issued on Mar. 15, 2012 in the prosecution history of U.S. Appl. No. 13/045,895.
International Search Report issued in relation with PCT Application PCT/US01/09409 on Aug. 28, 2001.

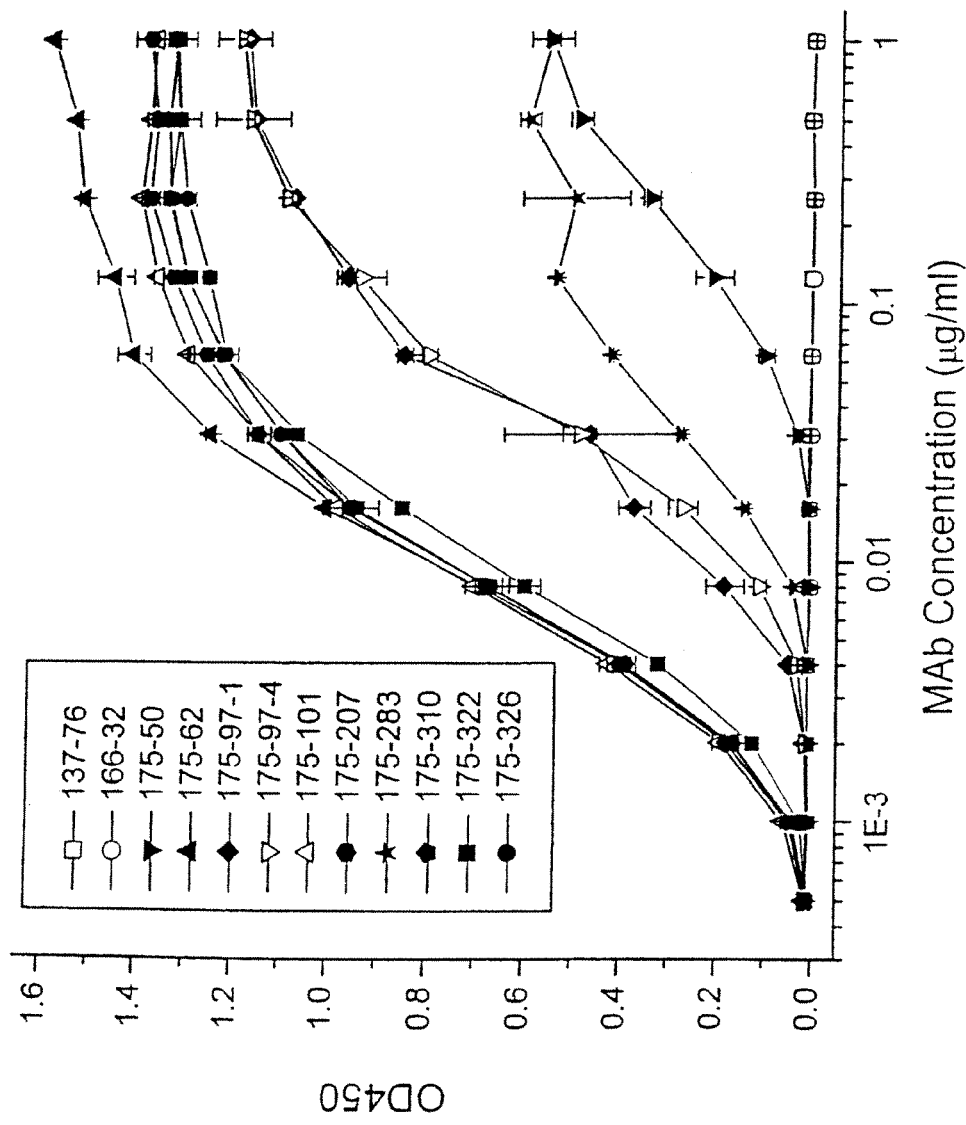
Fig. 1 Reactivity of MAbs with Human C2a

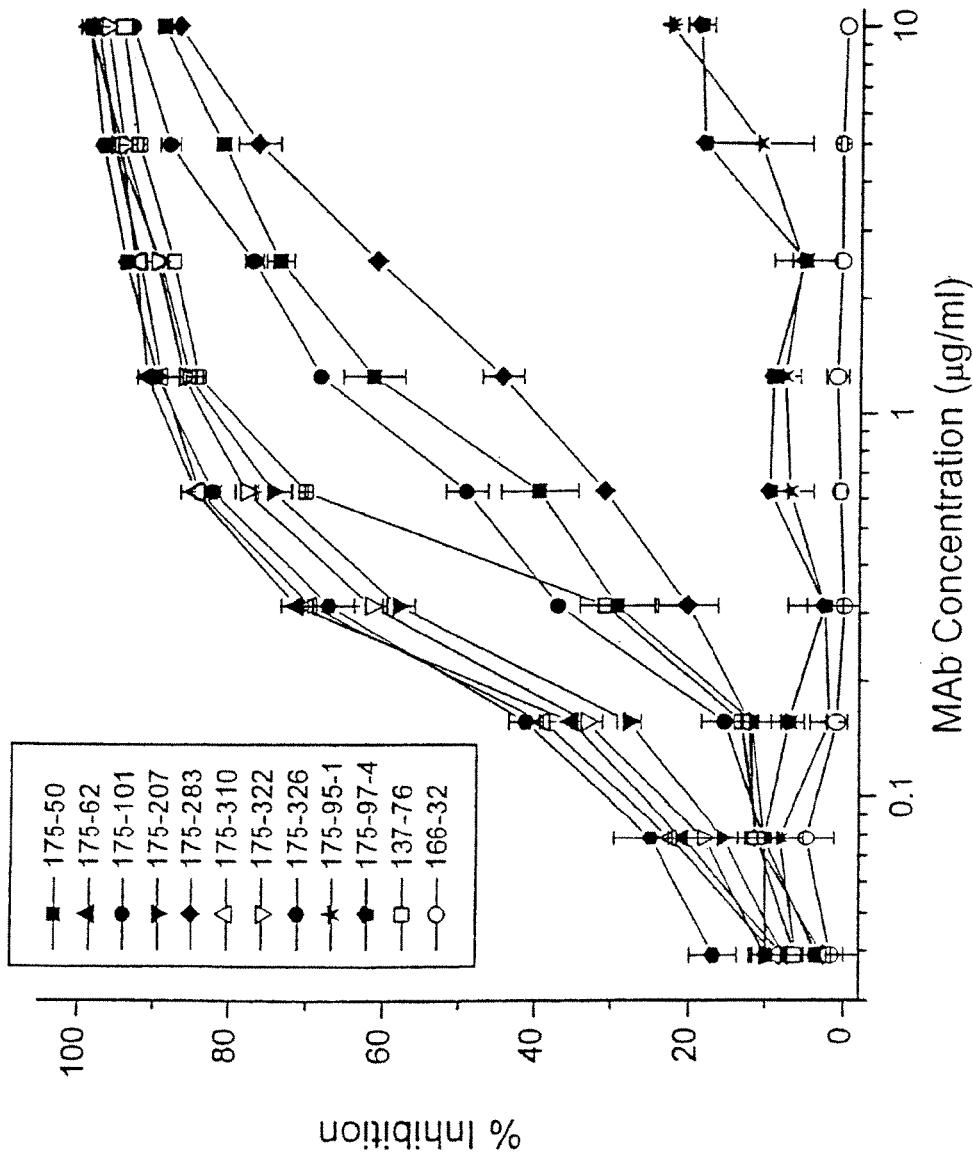
Fig. 2 Inhibition of CP Hemolysis by Anti-C2a MAbs

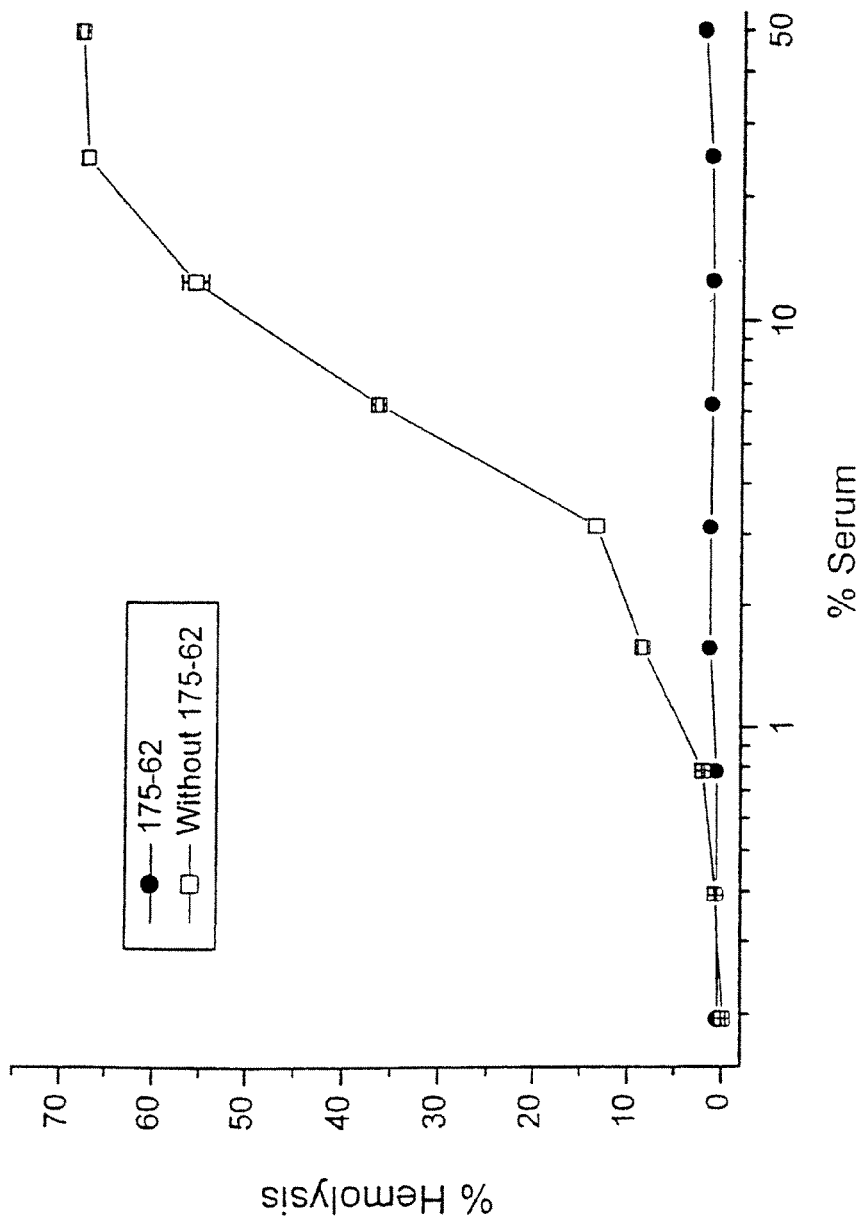
Fig. 3 Anti-C2a MAb 175-62 Completely Inhibits CP Hemolysis at a Molar Ratio of 1:2 (MAb to C2)

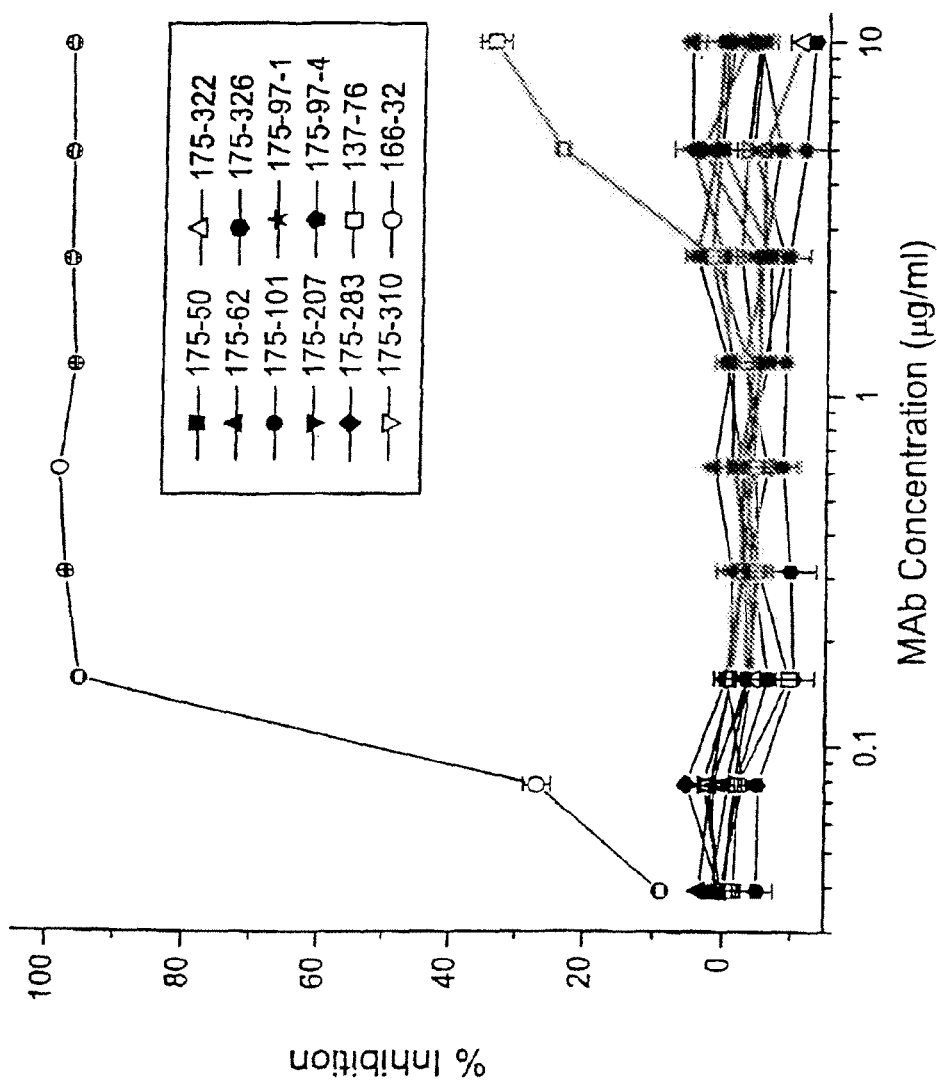

COMPLEMENT INHIBITORS AND USES THEREOF

This application is a divisional of U.S. application Ser. No. 13/045,895, filed Mar. 11, 2011, which is a continuation of U.S. application Ser. No. 10/908,738, filed May 24, 2005, now U.S. Pat. No. 7,927,592, which is a divisional of U.S. application Ser. No. 09/816,839, filed Mar. 23, 2001, now U.S. Pat. No. 6,998,468, which claims priority to U.S. Provisional Application No. 60/191,429, filed Mar. 23, 2000, the disclosure of each of which is incorporated herein by its entirety.

FIELD OF THE INVENTION

The present invention relates to inhibitor molecules specific to complement C2 and its activation fragment C2a, the use of such inhibitor molecules to block complement activation via the classical pathway and the lectin pathway, treatment of diseases associated with excessive complement activation, and the diagnostic determination of the amount of C2a present in a biological sample.

BACKGROUND OF THE INVENTION

The complement system is part of the innate immune system and consists of many components that act in a cascade fashion. This system plays a central role in both the clearance of immune complexes and the immune response to infectious agents, foreign antigens, virus-infected cells and tumor cells. However, complement is also involved in pathological inflammation and in autoimmune diseases. Therefore, inhibition of excessive or uncontrolled activation of the complement cascade could provide clinical benefit to patients with such diseases and conditions.

The complement system can be activated in three ways, either by one of the two primary activation pathways, designated the classical and the alternative pathways (V. M. Holers, In *Clinical Immunology: Principles and Practice*, ed. R. R. Rich, Mosby Press. 1996, 363-391), or by a third pathway, the lectin pathway activated by mannan-binding lectin (MBL) (M. Matsushita, *Microbiol. Immunol.*, 1996, 40: 887-893; M. Matsushita et al., *Immunobiol.*, 1998, 199: 340-347; T. Vorup-Jensen et al., *Immunobiol.*, 1998, 199: 348-357).

The classical pathway is a calcium/magnesium-dependent cascade, which is normally activated by the formation of antigen-antibody complexes. C1, the first enzyme complex in the cascade, is a pentamolecular complex consisting of C1q, 2 C1r molecules, and 2 C1s molecules. This complex binds to an antigen-antibody complex through the C1q domain to initiate the cascade. Once activated, C1s cleaves C4 resulting in C4b, which in turn binds C2. C2 is cleaved by C1s, resulting in the activated form, C2a, bound to C4b and forming the classical pathway C3 convertase.

The alternative pathway is a magnesium-dependent cascade and is antibody-independent. This pathway is activated by a variety of diverse substances including, e.g., cell wall polysaccharides of yeast and bacteria, and certain biopolymer materials. When the C3 protein binds on certain susceptible surfaces, it is cleaved to yield C3b thus initiating an amplification loop.

The lectin pathway involves complement activation by MBL through two serum serine proteases designated MASP-1 and MASP-2 (as opposed to C1r and C1s in the classical complement pathway). Like the classical complement pathway, the lectin complement pathway also requires C4 and C2 for activation of C3 and other terminal components further downstream in the cascade (C. Suankratay et al., *J. Immunol.*, 1998, 160: 3006-3013; Y. Zhang et al., *Immunopharmacol.*, 1999, 42: 81-90; Y. Zhang et al., *Immunol.*, 1999, 97: 686-692; C. Suankratay et al., *Clin. Exp. Immunol.*, 1999, 117: 442-448). Alternative pathway amplification is also required for lectin pathway hemolysis in human serum (C. Suankratay et al., *J. Immunol.*, 1998, 160: 3006-3013; C. Suankratay et al., *Clin. Exp. Immunol.*, 1998, 113: 353-359). In short, $Ca^{++}$-dependent binding of MBL to a mannan-coated surface triggers activation of C3 following C4 and C2 activation, and the downstream activation of C3 and the terminal complement components then require the alternative complement pathway for amplification.

Activation of the complement pathway generates biologically active fragments of complement proteins. e.g. C3a, C4a and C5a anaphylatoxins and sC5b-9 membrane attack complex (MAC), which mediate inflammatory activities involving leukocyte chemotaxis, activation of macrophages, neutrophils, platelets, mast cells and endothelial cells, vascular permeability, cytolysis, and tissue injury (R. Schindler et al., *Blood*, 1990, 76: 1631-1638; T. Wiedmer, *Blood*, 1991, 78: 2880-2886; M. P. Fletcher et al., *Am. J. Physiol.*, 1993, 265: H1750-1761).

C2 is a single-chain plasma protein of molecular weight of 102 kD, which is specific for the classical and the lectin complement pathways. Membrane bound C4b expresses a binding site which, in the presence of $Mg^{++}$, binds the proenzyme C2 near its amino terminus and presents it for cleavage by C1s (for the classical complement pathway) or MASP-2 (for the lectin complement pathway) to yield a 30 kD amino-terminal fragment, C2b, and a 70 kD carboxy-terminal fragment, C2a (S. Nagasawa et al., *Proc. Natl. Acad. Sci.* (*USA*), 1977, 74: 2998-3003). The C2b fragment may be released or remain loosely attached to C4b. The C2a fragment remains attached to C4b to form the C4b2a complex, the catalytic components of the C3 and C5 convertases of the classical and the lectin complement pathways. The enzymatic activity in this complex resides entirely in C2a, C4b acting to tether C2a to the activating surface.

Monoclonal antibodies (MAbs) to human C2 and its fragments C2a and C2b were made by immunizing mice with purified human C2 (E. I. Stenbaek et al., *Mol. Immunol.*, 1986, 23: 879-886; T. J. Oglesby et al., *J. Immunol.*, 1988, 141: 926-932). The novel anti-C2a MAbs of the present invention were made by immunizing mice with purified human C2a fragment and were shown to have inhibitory activity against the classical pathway complement activation (see below). These anti-C2a MAbs are distinct from the known anti-C2b MAb (see T. J. Oglesby et al., *J. Immunol.*, 1988, 141: 926-932) because they bind to different segments of C2 and inhibit the classical complement pathway by interfering the interaction between C2 and C4 (T. J. Oglesby et al., *J. Immunol.*, 1988, 141: 926-932). By virtue of this inhibition, the anti-C2a MAbs of the present invention are the first Mab demonstrated to be effective in inhibiting the classical complement pathway.

Targeting C2a and/or the C2a portion of C2 for complete inhibition of the classical and the lectin complement pathways has several advantages including, for example: (1) C2 and C2a are specific for the classical and the lectin complement pathways, and thus inhibition of C2 and/or C2a would achieve complete and selective inhibition of these two complement pathways without affecting the alternative complement pathway; (2) the concentration of C2 in human blood is one of the lowest (ca. 20 µg/ml) among other soluble complement components, therefore inhibitors of C2 or C2a would have a unique dose advantage; and (3) since C2a is the catalytic subunit of the C3 and C5 convertases, inhibition of C2 or the C2a portion of C2 would block the activation of C3 and C5.

The down-regulation of complement activation has been demonstrated to be effective in treating several disease indications in animal models and in ex vivo studies, e.g., systemic lupus erythematosus and glomerulonephritis (Y. Wang et al., *Proc. Natl. Acad. Sci.* (*USA*), 1996, 93: 8563-8568), rheumatoid arthritis (Y. Wang et al., *Proc. Natl. Acad. Sci.* (*USA*), 1995, 92: 8955-8959), in preventing inflammation associated with cardiopulmonary bypass and hemodialysis (C. S. Rinder et al., *J. Clin. Invest.*, 1995, 96: 1564-1572; J. C. K. Fitch et al., *Circulation*, 1999, 100: 2499-2506; H. L. Lazar et al., *Circulation*, 1999, 100: 1438-1442), hyperacute rejection in organ transplantation (T. J. Kroshus et al., *Transplantation*, 1995, 60: 1194-1202), myocardial infarction (J. W. Homeister et al., *J. Immunol.*, 1993, 150: 1055-1064; H. F. Weisman et al., *Science*, 1990, 249: 146-151), reperfusion injury (E. A. Amsterdam et al., *Am. J. Physiol.*, 1995, 268: H448-H457), and adult respiratory distress syndrome (R. Rabinovici et al., *J. Immunol.*, 1992, 149: 1744-1750). In addition, other inflammatory conditions and autoimmune/immune complex diseases are also closely associated with complement activation (V. M. Holers, ibid., B. P. Morgan. *Eur. J. Clin. Invest.*, 1994, 24: 219-228), including thermal injury, severe asthma, anaphylactic shock, bowel inflammation, urticaria, angioedema, vasculitis, multiple sclerosis, psoriasis, dermatomyositis, myasthenia gravis, membranoproliferative glomerulonephritis, and Sjögren's syndrome.

SUMMARY OF THE INVENTION

The present invention includes inhibitor molecules having a binding region specific for C2a or the C2a portion of C2. The inhibitor molecule may be an antibody or a homologue, analogue or fragment thereof, a peptide, an oligonucleotide, a peptidomimetic or an organic compound. Antibody fragments can be Fab, F(ab')$_2$, Fv or single chain Fv. The inhibitor molecule may be in the form of a pharmaceutical composition.

One embodiment of the present invention includes an inhibitor molecule comprising a monoclonal antibody. The antibody may be chimeric, deimmunized, humanized or human antibody. Specifically, the monoclonal antibody may be the monoclonal antibody designated 175-62.

Another embodiment of the invention is a hybridoma producing the monoclonal antibody 175-62.

Another embodiment of the invention includes monoclonal antibodies or a fragment, analogue or homologue thereof, or a peptide, oligonucleotide, peptidomimetic or an organic compound which bind to the same epitope as the antibody 175-62. These antibodies can include Fab, F(ab')$_2$, Fv or single chain Fv, and may be chimeric, deimmunized, humanized or human antibody. In addition, the present invention includes cell lines that produces the monoclonal antibody or fragment thereof that bind to the same epitope as the antibody 175-62.

The present invention also includes molecules that inhibit complement activation by inhibiting both the classical and lectin complement pathways. The preferred molecules of the present invention inhibit complement activation at a molar ratio of inhibitor molecule to C2 at 1:2.

Another embodiment of the present invention includes a method of treating a disease or condition that is mediated by excessive or uncontrolled activation of the complement system by administering, in vivo or ex vivo, an inhibitor molecule that specifically binds C2a or the C2a portion of C2.

One example of a Mab, designated 175-62, that binds to C2a and blocks its ability to activate complement was generated as described below. The hybridoma producing this antibody was deposited at the American Type Culture Collection, 10801 University Blvd., Manassas, Va. 20110-2209, under Accession Number PTA-1553, on Mar. 22, 2000.

BRIEF DESCRIPTION OF THE FIGURES

FIG. 1 shows the binding of anti-C2a MAbs (175 series), anti-C5 Mab (137-76), and anti-factor D Mab (166-32) to purified human C2a in an ELISA. The Y-axis represents the reactivity of the MAbs with C2a expressed as optical density (OD) at 450 nm and the X-axis represents the concentration of the MAbs. MAb 175-62 shows the strongest reactivity with C2a.

FIG. 2 shows the inhibition of classical pathway hemolysis of sensitized chicken red blood cells (RBCs) by anti-C2a MAbs in the presence of 3% human serum. The controls were anti-factor D Mab (166-32) and the anti-05 MAb (137-76). Anti-factor D Mab 166-32 specifically inhibits the alternative complement pathway, therefore it does not inhibit the classical pathway hemolysis. The Y-axis represents the % hemolysis inhibition, as further described in the text. The X-axis represents the concentration of the MAbs. All anti-C2a MAbs strongly inhibit classical pathway hemolysis.

FIG. 3 shows that anti-C2a MAb 175-62 inhibits classical pathway (CP) hemolysis at a molar ratio of 1:2 (MAb 175-62 to C2). The filled circles represent MAb 175-62. The open squares represent hemolysis in the absence of MAb 175-62. The Y-axis represents the % hemolysis inhibition. The X-axis represents the concentration of serum. The classical pathway hemolytic activity of C2 (0.2 µM) in normal human serum is completely inhibited when the serum was pre-treated with 0.1 µM of MAb 175-62.

FIG. 4 shows an assay for testing the inhibition of alternative pathway (AP) hemolysis of unsensitized rabbit RBCs by anti-C2a, anti-factor D and anti-05 MAbs, in the presence of 10% human serum. The Y-axis represents the % hemolysis inhibition, as further described in the text. The X-axis represents the concentration of the MAbs. The data illustrate that none of the anti-C2a MAbs inhibit the alternative complement pathway.

DETAILED DESCRIPTION

The inhibitor molecules of the present invention include monoclonal antibodies as well as homologues, analogues and modified or derived forms thereof, including immunoglobulin fragments such as Fab, F(ab')$_2$, and Fv, and single chain antibodies. Also included are small molecules including peptides, oligonucleotides, peptidomimetics and organic compounds.

One embodiment of the invention includes anti-C2a MAbs, which can be raised by immunizing rodents (e.g. mice, rats, hamsters and guinea pigs) with either (1) native C2a derived from enzymatic digestion of C2 purified from human plasma or serum, or (2) recombinant C2a or its fragments expressed by either eukaryotic or prokaryotic systems. Other animals can be used for immunization, e.g. non-human primates, transgenic mice expressing human immunoglobulins, and severe combined immunodeficient (SCID) mice transplanted with human B-lymphocytes.

Hybridomas can be generated by conventional procedures by fusing B-lymphocytes from the immunized animals with myeloma cells (e.g., Sp2/0 and NS0), as described by G. Köhler and C. Milstein (*Nature*, 1975, 256: 495-497). In addition, anti-C2a antibodies can be generated by screening recombinant single-chain Fv or Fab libraries from human B-lymphocytes in a phage-display system. The specificity of the MAbs to human C2a can be tested by enzyme linked immunosorbent assay (ELISA), Western immunoblotting, or other immunochemical techniques.

The inhibitory activity on complement activation of antibodies identified in the screening process can be assessed by hemolytic assays using either unsensitized rabbit or guinea pig RBCs for the alternative complement pathway, or sensitized chicken or sheep RBCs for the classical complement pathway. Those hybridomas that exhibit an inhibitory activity specific for the classical complement pathway are cloned by limiting dilution. The antibodies are purified for characterization for specificity to human C2a by the assays described above.

When treating inflammatory or autoimmune diseases in humans, the anti-C2a antibodies may be chimeric, deimmunized, humanized or human antibodies. Such antibodies can reduce immunogenicity, thereby avoiding a human/anti-mouse antibody (HAMA) response. It is preferable that the antibody be IgG4, IgG2, or other genetically mutated IgG or IgM which does not augment antibody-dependent cellular cytotoxicity (S. M. Canfield et al., *J. Exp. Med.* 1991, 173: 1483-1491) and complement mediated cytolysis (Y. Xu et al., *J. Biol. Chem.*, 1994, 269: 3468-3474; V. L. Pulito et al., *J. Immunol.*, 1996, 156: 2840-2850).

Chimeric antibodies are produced by recombinant processes well known in the art, and have an animal variable region and a human constant region. Humanized antibodies have a greater degree of human peptide sequences than do chimeric antibodies. In a humanized antibody, only the complementarity determining regions (CDRs), which are responsible for antigen binding and specificity, are animal derived. The amino acid sequence corresponding to the animal antibody, and substantially all of the remaining portions of the molecule (except, in some cases, small portions of the framework regions within the variable region) are human derived and correspond in amino acid sequence to a human antibody. See, e.g., L. Riechmann et al. *Nature,* 1988, 332: 323-327; G. Winter, U.S. Pat. No. 5,225,539; C. Queen et al., U.S. Pat. No. 5,530,101.

Deimmunized antibodies are antibodies in which the T-helper epitopes have been eliminated, as described in International Patent Application PCT/GB98/01473. They have either reduced or no immunogenicity when administered in vivo.

Human antibodies can be made by several different methods, including the use of human immunoglobulin expression libraries (Stratagene Corp., La Jolla, Calif.) to produce fragments of human antibodies (VH, VL, Fv, Fd, Fab, or $F(ab')_2$) to construct whole human antibodies using techniques similar to those for producing chimeric antibodies. Human antibodies can also be produced in transgenic mice with a human immunoglobulin genome. Such mice are available from Abgenix, Inc., Fremont, Calif., and Medarex, Inc., Annandale, N.J.

One can also create single peptide chain binding molecules in which the heavy and light chain Fv regions are connected. Single chain antibodies ("scFv") and the method of their construction are described in U.S. Pat. No. 4,946,778. Alternatively, Fab can be constructed and expressed by similar means (M. J. Evans et al., *J. Immunol. Meth.,* 1995, 184: 123-138).

Antibodies, fragments thereof, and single chain antibodies that are wholly or partially derived from human are less immunogenic than wholly murine MAbs, and therefore, less likely to evoke an immune or allergic response. Consequently, human-derived antibodies are better suited for in vivo administration in humans than wholly animal antibodies, especially when repeated or long-term administration is necessary. In addition, smaller size antibody fragments may help improve tissue bioavailability, which may offer better dose accumulation in certain disease indications.

Based on the molecular structures of the variable regions of the anti-C2a antibodies, one can use molecular modeling and rational molecular design to generate and screen small molecules that mimic the molecular structures of the binding region of the antibodies and inhibit the activities of C2a. These small molecules can be peptides, peptidomimetics, oligonucleotides, or organic compounds. The mimicking molecules can be used as inhibitors of complement activation in inflammatory indications and autoimmune diseases. Alternatively, one can use large-scale screening procedures commonly used in the field to isolate suitable small molecules from libraries of combinatorial compounds.

Applications of the Anti-C2a Molecules

The anti-C2a binding molecules, antibodies, and fragments of the present invention can be administered to patients in an appropriate pharmaceutical formulation by a variety of routes, including, but not limited, intravenous infusion, intravenous bolus injection, and intraperitoneal, intradermal, intramuscular, subcutaneous, intranasal, intratracheal, intraspinal, intracranial, and oral routes. Such administration enables them to bind to endogenous C2a or C2 and thus inhibit the generation of C3b, C3a and C5a anaphylatoxins, and C5b-9.

The estimated dosage of such antibodies and molecules is between 10 and 500 µg/ml of serum. The actual dosage can be determined in clinical trials following the conventional methodology for determining optimal dosages, i.e., administering various dosages and determining which is most effective.

The anti-C2a inhibitor molecules can function to inhibit in vivo complement activation and inflammatory manifestations that accompany it, such as recruitment and activation of macrophages, neutrophils, platelets, mast cells and endothelial cells, edema, and tissue damage. These inhibitor molecules can be used for treatment of diseases or conditions that are mediated by excessive or uncontrolled activation of the complement system. These include, but are not limited to: (1) tissue damage due to ischemia-reperfusion following acute myocardial infarction, aneurysm, stroke, hemorrhagic shock, crush injury, multiple organ failure, hypovolemic shock and intestinal ischemia; (2) inflammatory disorders, such as, burns, endotoxemia and septic shock, adult respiratory distress syndrome, cardiopulmonary bypass, hemodialysis, anaphylactic shock, severe asthma, angioedema, Crohn's disease, psoriasis, dermomyositis, sickle cell anemia, poststreptococcal glomerulonephritis, and pancreatitis; (3) transplant rejections, such as, hyperacute xenograft rejection; and (4) adverse drug reactions, such as, drug allergy, IL-2 induced vascular leakage syndrome, and radiographic contrast media allergy. Autoimmune disorders including, but not limited to, systemic lupus erythematosus, myasthenia gravis, rheumatoid arthritis, Alzheimer's disease and multiple sclerosis, may also be treated with the inhibitor molecules of the invention.

The anti-C2a inhibitor molecules can also be used diagnostically to ascertain the presence of, or to measure, C2a in a tissue specimen or a body fluid sample, such as serum, plasma, urine or spinal fluid. In this application, common assay formats can be used, such as immunohistochemistry or ELISA, respectively. Such diagnostic tests could be useful in determining whether certain individuals are either deficient in or overproduce C2a.

Animal Models of the Therapeutic Efficacy of C2a Inhibitors

The therapeutic activity of C2a inhibitor molecules in various disease indications described above can be confirmed by using available animal models for various inflammatory and autoimmune manifestations.

Animal models relevant to various complement-related clinical diseases in humans can be used to confirm the in vivo efficacy of C2a inhibitors. These include, but are not limited to: myocardial ischemia/reperfusion injury (H. F. Weisman et al., Science, 1990, 249: 146-151); myocardial infarction (J. W. Homeister et al., J. Immunol., 1993, 150: 1055-1064), systemic lupus erythematosus and glomerulonephritis (S. K. Datta. Meth. Enzymol., 1988, 162: 385-442; D. J. Salvant et al., Meth. Enzymol., 1988, 162: 421-461), rheumatoid arthritis (Y. Wang et al., Proc. Natl. Acad. Sci. (USA), 1995, 92: 8955-8959), adult respiratory distress syndrome (R. Rabinovici et al. J. Immunol., 1992, 149: 1744-1750), hyperacute rejection in organ transplantation (T. J. Kroshus et al., Transplantation, 1995, 60: 1194-1202), burn injury (M. S. Mulligan et al., J. Immunol., 1992, 148: 1479-1485), cardiopulmonary bypass (C. S. Rinder et al., J. Clin. Invest., 1995, 96: 1564-1572).

Example 1

Generation of Anti-C2a MAb Hybridomas

Eight to twelve-week old male A/J mice (Harlan, Houston. TX) were subcutaneously injected with 20 µg of C2a in complete Freund's adjuvant (Difco Laboratories, Detroit, Mich.) in 200 µl of phosphate-buffered saline (PBS) pH 7.4. The C2a was generated by enzymatic digestion using C1s (Advanced Research Technologies, San Diego, Calif.) conjugated to CNBr-activated Sepharose® 6 MB (Pharmacia Biotech, Piscataway, N.J.), similar to the procedure described in T. J. Oglesby, J. Immunol., 1988, 141: 926-931. The resulting C2a was then purified by passage through a Sephadex®-200 size-exclusion HPLC column. The C2a preparation was tested to be >95% pure by sodium dodecylsulphate (SDS)-polyacrylamide gel electrophoresis (PAGE). C2 was purified from human serum (Advanced Research Technologies).

At two-week intervals, mice were twice injected subcutaneously with 20 µg of C2a in incomplete Freund's adjuvant. Then, two weeks later, three days prior to sacrifice, the mice were again injected intraperitoneally with 20 µg of the same antigen in PBS.

For each hybridoma, single cell suspensions were prepared from the spleen of an immunized mouse and fused with Sp2/0 myeloma cells. $5 \times 10^8$ of the Sp2/0 and $5 \times 10^8$ spleen cells were fused in a medium containing 50% polyethylene glycol (M. W. 1450) (Kodak, Rochester, N.Y.) and 5% dimethylsulfoxide (Sigma Chemical Co., St. Louis, Mo.). The cells were then adjusted to a concentration of $1.5 \times 10^5$ spleen cells per 200 µl of the suspension in Iscove medium (Gibco, Grand Island, N.Y.), supplemented with 10% fetal bovine serum, 100 units/ml of penicillin, 100 µg/ml of streptomycin, 0.1 mM hypoxanthine, 0.4 µM aminopterin, and 16 µM thymidine. Two hundred µl of the cell suspension were added to each well of about fifty 96-well microculture plates. After about ten days, culture supernatants were withdrawn for screening for reactivity with purified C2a in ELISA.

Wells of Immulon® 2 (Dynatech Laboratories, Chantilly, Va.) microtest plates were coated by adding 50 µl of purified human C2a at 50 ng/ml overnight at room temperature. The low concentration of C2a used for coating enabled the selection of high-affinity antibodies. After the coating solution was removed by flicking the plate, 200 µl of BLOTTO (non-fat dry milk) in PBS was added to each well for one hour to block the non-specific sites. An hour later, the wells were then washed with a buffer PBST (PBS containing 0.05% Tween® 20). Fifty microliters of culture supernatants from each fusion well were collected and mixed with 50 µl of BLOTTO and then added to the individual wells of the microtest plates. After one hour of incubation, the wells were washed with PBST. The bound murine antibodies were then detected by reaction with horseradish peroxidase (HRP)-conjugated goat anti-mouse IgG (Fc specific) (Jackson ImmunoResearch Laboratories, West Grove, Pa.) and diluted at 1:2,000 in BLOTTO. Peroxidase substrate solution containing 0.1% 3,3,5,5 tetramethyl benzidine (Sigma) and 0.0003% hydrogen peroxide (Sigma) was added to the wells for color development for 30 minutes. The reaction was terminated by addition of 50 µl of 2M $H_2SO_4$ per well. The OD at 450 nm of the reaction mixture was read with a BioTek ELISA Reader (BioTek Instruments, Winooski, Vt.).

The culture supernatants from the positive wells were then tested for inhibition of classical pathway hemolysis of sensitized chicken RBCs by pre-titered human serum (3%) by the method described below. The cells in those positive wells were cloned by limiting dilution. The MAbs were tested again for reactivity with C2a and C2 in the ELISA. The selected hybridomas were grown in spinner flasks and the spent culture supernatant collected for antibody purification by protein A affinity chromatography. Ten MAbs were tested to be reactive with human C2a in ELISA. These MAbs are designated MAbs 175-50, 175-62, 175-97-1, 175-97-4, 175-101, 175-207, 175-283, 175-310, 175-322, and 175-326. As seen in FIG. 1, MAb 175-62, MAb 175-101, MAb 175-207, MAb 175-310, MAb 175-322, and MAb 175-326 reacted strongly with human C2a in ELISA. In particular, MAb 175-62 shows the strongest reactivity with C2a among these binders. Interestingly, it binds weakly to immobilized C2 in ELISA.

Example 2

Inhibition of Complement-Activated Hemolysis

To study the functional activity of the anti-C2a MAbs in inhibiting complement activation in vitro, two hemolytic assays were used.

For the classical pathway, chicken RBCs ($5 \times 10^7$ cells/trip, in gelatin/veronal-buffered saline ($GVB^{++}$) containing 0.5 mM $MgCl_2$ and 0.15 mM $CaCl_2$, were sensitized with purified rabbit anti-chicken RBC immunoglobulins at 8 µg/ml (Inter-Cell Technologies, Hopewell, N.J.) for 15 minutes at 4° C. The cells were then washed with $GVB^{++}$. The washed cells were re-suspended in the same buffer at $1.7 \times 10^8$ cells/ml. In each well of a round-bottom 96-well microtest plate, 50 µl of normal human serum (6%) was mixed with 50 µl of $GVB^{++}$ or serially diluted test MAb, then 30 µl of the washed sensitized chicken RBC suspension were added to the wells containing the mixtures. Fifty microliters of normal human serum (6%) was mixed with 80 µl of $GVB^{++}$ to give the serum color background. The final mixture was incubated at 37° C. for 30 minutes. The plate was then shaken on a micro-test plate shaker for 15 seconds, followed by centrifugation at 300×g for 3 minutes. Supernatants (80 µl) were collected and transferred to wells on a flat-bottom 96-well microtest plates for measurement of OD at 405 nm. The percent inhibition of hemolysis is defined as 100×[(OD without MAb−OD serum color background)−(OD with MAb−OD serum color background)]/(OD without MAb−OD serum color background).

The data in FIG. 2 show that the anti-C2a MAbs 175-62, 175-207, 175-310, 175-322, and 175-326 strongly inhibit classical pathway hemolysis. The anti-C5 MAb 137-76 also inhibits the hemolysis, but not the anti-factor D MAb 166-32, which is specific for inhibition of the alternative complement pathway.

The stoichiometric ratio of inhibition between MAb 175-62 and C2 in human serum by the classical pathway hemolytic assays was also measured as described above. Different molar ratios of MAb 175-62 to C2 were tested in the assays by combining normal human serum (containing 20 µg/ml or 0.2 µM of C2) with 0.4 µM, 0.2 µM, or 0.1 µM of MAb 175-62. The control was normal human serum treated with equal volume of GVB$^{++}$. The mixtures were incubated at room temperature for 15 minutes. The mixtures were then serially diluted in GVB$^{++}$. One hundred microliters of the diluted serum samples were added to each well of a round-bottom 96-well plate in duplicate. Thirty microliters of sensitized chicken RBCs were then added to each well for incubation as described above. The final mixture was incubated at 37° C. for 30 minutes. The plate was then shaken on a microtest plate shaker for 15 seconds, followed by centrifugation at 300×g for 3 minutes. Supernatants (80 µl) were collected and transferred to wells on a flat-bottom 96-well microtest plates for measurement of OD at 405 nm.

The data in FIG. 3 show that the classical pathway hemolytic activity of C2 (0.2 µM) in normal human serum is completely inhibited when the serum was pre-treated with 0.1 µM of MAb 175-62. Therefore, MAb 175-62 inhibits human C2 at a molar ratio of 1:2 (Mab 175-62 to C2). In other words, MAb 175-62 is a very high-affinity anti-C2 antibody. Each of the two antigen binding sites in a molecule of MAb 175-62 can bind one molecule of C2.

For the alternative pathway, unsensitized rabbit RBCs were washed three times with gelatin/veronal-buffered saline (GVB/Mg-EGTA) containing 2 mM MgCl$_2$ and 1.6 mM EGTA. EGTA at a concentration of 10 mM was used to inhibit the classical pathway (K. Whaley et al., in A. W. Dodds (Ed.), *Complement: A Practical Approach*. Oxford University Press, Oxford, 1997, pp. 19-47). The procedures of the assay were similar to those of the classical pathway hemolysis as described above. The final concentration of human serum was 10%.

The data in FIG. 4 show that none of the anti-C2a MAbs inhibit the alternative pathway hemolysis, whereas anti-factor D MAb 166-32 effectively inhibits the hemolysis and anti-C5 MAb 137-76 moderately inhibits the hemolysis. Together with the results in FIGS. 2 and 3, the anti-C2a MAbs have been shown to be specific for the classical complement pathway.

What is claimed is:

1. A method of treating a disease or condition that is mediated by excessive or uncontrolled activation of the complement system comprising administering an antibody that binds to C2a or the C2a portion of C2 or a C2a binding fragment thereof, wherein the molar ratio of antibody to C2 is one antibody molecule to two C2 or C2a molecules and the antibody inhibits both the classical and the lectin complement pathways, wherein the disease or condition is rheumatoid arthritis.

2. The method of claim 1, wherein the antibody or C2a binding fragment thereof is administered by intravenous infusion, intravenous bolus injection, intraperitoneal, intradermal, intramuscular, subcutaneous, intranasal, intratracheal, intraspinal, intracranial, or orally.

3. The method of claim 1, wherein the antibody binds to the same epitope as the monoclonal antibody 175-62.

4. The method of claim 1, wherein the antibody is a monoclonal antibody.

5. The method of claim 1, wherein the antibody is a chimeric, deimmunized, humanized or human antibody.

6. The method of claim 1, wherein the C2a binding fragment is a Fab, F(ab')$_2$, Fv or single chain Fv.

7. The method of claim 1, wherein the antibody is a monoclonal antibody designated 175-62 produced by the hybridoma cell line deposited under ATCC Accession Number PTA-1553.

8. The method of claim 1, wherein the inhibition of complement pathways is determined in vitro.

* * * * *